(12) United States Patent
Payne et al.

(10) Patent No.: US 6,376,232 B1
(45) Date of Patent: Apr. 23, 2002

(54) MICROORGANISM ANALYSIS MEANS

(75) Inventors: Peter Alfred Payne, Knutsford; Krishna Chandra Persaud, Cheadle; Allan John Syms, Lach Dennis, all of (GB)

(73) Assignee: Osmetech PLC, Cheshire (GB)

( * ) Notice: Subject to any disclaimer, the term of this patent is extended or adjusted under 35 U.S.C. 154(b) by 0 days.

(21) Appl. No.: 09/380,633

(22) PCT Filed: Mar. 6, 1998

(86) PCT No.: PCT/GB98/00509

§ 371 Date: Oct. 7, 1999

§ 102(e) Date: Oct. 7, 1999

(87) PCT Pub. No.: WO98/39409

PCT Pub. Date: Sep. 11, 1998

(30) Foreign Application Priority Data

Mar. 6, 1997 (GB) .............................. 9704626
Mar. 18, 1997 (GB) .............................. 9705514

(51) Int. Cl.⁷ .............................. C12M 1/34; C12Q 1/24
(52) U.S. Cl. .................. 435/287.5; 435/30; 435/34; 435/288.1; 435/309.1
(58) Field of Search .................. 435/287.1, 287.5, 435/287.7, 287.9, 288.1, 288.6, 297.2, 300.1, 309.1, 29, 30, 31, 34; 73/234.1, 863.23; 422/80

(56) References Cited

U.S. PATENT DOCUMENTS

| | | | |
|---|---|---|---|
| 2,923,669 A | * 2/1960 | Poitras | 435/288.6 |
| 3,324,855 A | 6/1967 | Heimlich | 128/269 |
| 3,918,435 A | * 11/1975 | Beall et al. | |
| 4,003,240 A | * 1/1977 | Durbin | 73/1 G |
| 4,073,691 A | * 2/1978 | Ahnell et al. | |
| 4,553,553 A | 11/1985 | Homann et al. | 128/749 |
| 4,707,450 A | * 11/1987 | Nason | |
| 4,953,560 A | * 9/1990 | Samuels | |
| 4,962,036 A | * 10/1990 | Cermak et al. | 435/288.6 |
| 5,047,331 A | 9/1991 | Swaine et al. | 435/29 |
| 5,051,360 A | 9/1991 | Waters | 435/34 |
| 5,440,942 A | * 8/1995 | Hubbard | 73/864.91 |
| 5,814,474 A | * 9/1998 | Berndt | 435/34 |

FOREIGN PATENT DOCUMENTS

| | | |
|---|---|---|
| WO | 0088971 | 9/1983 |
| WO | 0357892 | 3/1990 |
| WO | WO 93/12421 | 6/1993 |
| WO | 07-260770 | * 10/1995 |

OTHER PUBLICATIONS

International Search Report; PCT/GB98/00509; Jun. 30, 1998; A. Coucke.

* cited by examiner

Primary Examiner—William H. Beisner
(74) Attorney, Agent, or Firm—Fish & Richardson P.C.

(57) ABSTRACT

A microorganism analyzer has a flow-through arrangement into which a microorganism-containing sample may be introduced, and a headspace connected or connectible to a gas analyzer. The headspace is connected to the flow-through arrangement so as to be affected by the sample.

22 Claims, 1 Drawing Sheet

MICROORGANISM ANALYSIS MEANS

Figure 1:
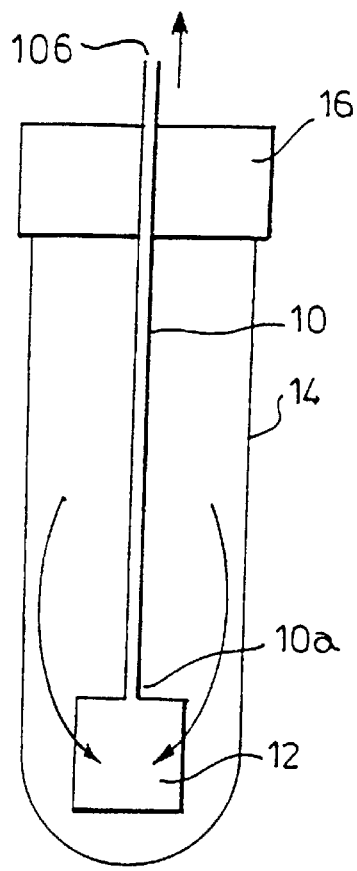

This invention relates to the detection of microorganisms, more particularly to an apparatus for obtaining samples of microorganisms.

International Publication WO 95/33848 describes a method for identifying bacteria on the basis of characteristic gases and vapours emitted as by-products of bacterial metabolism. The gases and vapours are detected by an array of gas sensing devices, in particular arrays based on semi-conducting organic polymers.

One very important source of such bacteria are samples obtained in a swab of some sort. The present invention provides a single apparatus having a dual use i) as a swab and ii) as a integral part of a gas sampling system for subsequent investigation by gas analysis.

For the avoidance of doubt, the term "gas" is understood to encompass any species in the gas phase, including vapours from volatile liquids.

According to the invention there is provided microorganism analysis means comprising:

a flow-through arrangement into which a microorganism-containing sample may be introduced;

a headpsace connected or connectible to gas analysis means;

the headpsace being connected to the flow-through arrangement so as to be affected by the sample.

The analysis means may comprise:

a tubular member; and porous means disposed at one end of said tubular member and communicating therewith so that gas may be flowed through said swab means and said tubular member, the gas flow carrying gases evolved from said microorganism-containing sample therein.

The apparatus may further comprise a receptacle into which said tubular member and swab means may be disposed.

The swab means may comprise a polyethylene mesh or a porous ceramic.

The apparatus may farther comprise a culturing medium, which may be a gel disposed on the surface of the swab means. The gel may be an agar gel.

The swab means may include a layer of cotton wool or gauze.

The tubular member may be disposed in a cap, the cap forming a seal with the receptacle when the tubular member and swab means are disposed therein. The cap may comprise a gas port.

Gases evolved from said microorganism-containing sample may be entrained in a flow of gas which enters the receptacle via the gas port and exits the receptacle via the tubular member.

Gases evolved from said microorganism-containing sample may be entrained in a flow of gas which enters the receptacle via the tubular member and exits the receptacle via the gas port. The swab means may be disposed in a liquid culturing medium.

The flow-through arrangement may comprise a filter on which microorganisms may be collected from a sample flowing through the arrangement. The filter may be a micro-gauge filter.

The flow-through arrangement may, however, comprise an affinity column, which may be connected to a headspace for gas analysis or which may be subject to a washing flow carrying the released microorganism to a headspace generating arrangement.

Figure 2:
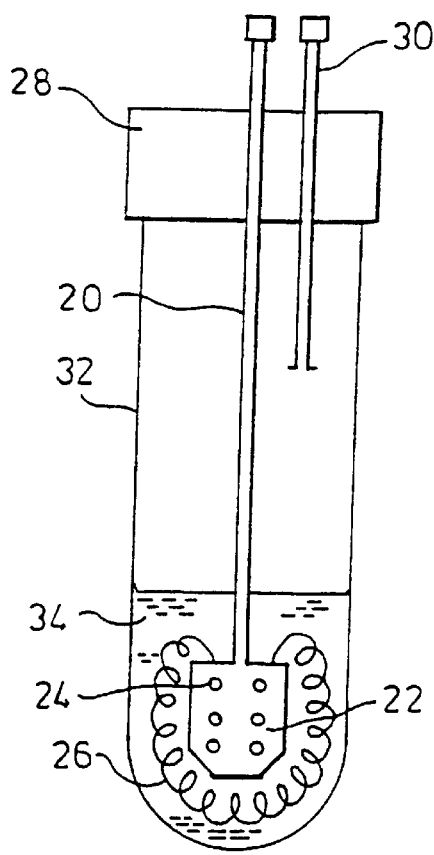
Figure 3:
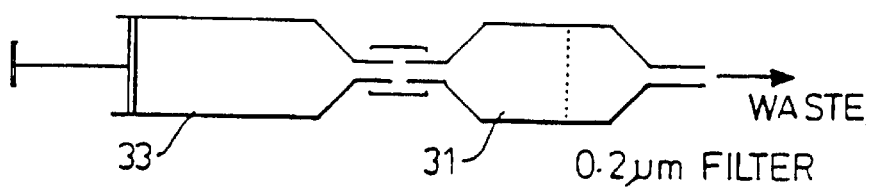
Figure 4:
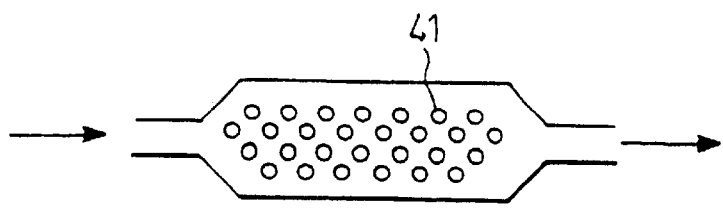

Apparatus in accordance with the invention will now be described with reference to the accompanying drawings, in which:

FIG. 1 shows a first embodiment of the invention;
FIG. 2 shows a second embodiment of the invention;
FIG. 3 shows a third embodiment of the invention; and
FIG. 4 shows a fourth embodiment of the invention.

FIG. 1 shows a first embodiment of the invention for obtaining a sample of bacteria and sampling gases evolved therefrom comprising:

a tubular member 10; and porous swab means 12 disposed at one end 10a of said tubular member 10 and communicating therewith so that a gas may be flowed through said swab means 12 and said tubular member 10, the gas flow carrying gases evolved from said sample of bacteria therein.

The swab means 12 is first used to obtain a sample of bacteria in the usual manner from, for example, a body part of a patient. It is advantageous in this regard that the tubular member 10 acts as a convenient handle whilst performing this task.

Usually, thereafter, the tubular member 10 and swab means 12 are disposed in a receptacle 14.

The swab means 12 is a porous frit that permits passage of gases therethrough. The swab means may comprise a polyethylene mesh or a porous ceramic.

It is advantageous—although not always essential—that the apparatus further comprises a culturing medium. As will become apparent later, a liquid culturing medium is not suitable with the first embodiment. However, a gel disposed on the surface of the swab means 12 is suitable. An example is an agar gel, which acts as a semi-permeable membrane.

The apparatus performs a dual role, since it is adapted to provide sampling of gases evolved by the bacterial sample. The gases are eventually introduced to a gas sensing device. In the embodiment of FIG. 1, the gas is pumped, in the direction indicated by the arrows, through the tubular member 10 towards the gas sensing device (not shown).

The tubular member 10 is advantageously disposed in a cap 16, the cap 16, forming a seal with the receptacle 14 when the tubular member 10 and swab means 12 are disposed therein. In this way a sample headspace is created. It may be possible to operate without a cap 16, although in general, of course, exposure of the bacteria to the atmosphere is to be avoided. In this vein, the end 10b of the tubular might be provided with a polymer or elastomer seal which is broken before sampling or which breaks if a pre-defined positive pressure is produced in the receptacle 14.

Alternatively, the cap 16 can comprise a gas port, which in this example would act as a gas inlet. A suitable carrier gas, such as nitrogen, would then be flowed into the receptacle 14, gases evolved by the bacteria carried therein. It may be possible to use the tubular member 10 as a gas inlet and the gas port as an outlet.

FIG. 2 shows a second embodiment of the invention comprising a tubular member 20 and porous swab means 22. The tubular member 20 and swab means 22 are moulded as one piece in plastic. The swab means 22 comprise a plurality of apertures 24 which communicate with the hollow core of the tubular member 20. A polyethylene mesh or a porous ceramic might be used as swab means 22 instead.

The swab means 22 further comprises a layer of cotton wool or gauze 26.

The tubular member 20 is disposed in a cap 28, the cap 28 comprising a gas port 30. After using the swab means 22 to obtain a sample of bacteria, the unit comprising the tubular member 20, swab means 22 and cap 28 are disposed in a receptacle 32, the cap forming a seal therewith.

The receptacle advantageously contains a liquid culturing medium 34.

The tubular member 20 and gas port 30 are adapted for connection to a suitable gas sampling system, in which gas is pumped from the gas port 30 across a gas sensing device (not shown). Gas—which might be atmospheric air, or an inert carrier gas such as nitrogen—enters the receptacle 32 via the tubular member 20. The gas flows out of the apertures 24 and bubbles through the culturing medium 34. Gases evolved by the sample of bacteria are thus carried in the gas flow.

The gases evolved by the sample of bacteria may be detected by any suitable gas sensor arrangement. A preferred form is an array of gas sensors, most preferably an array of semiconducting organic polymer gas sensors, such as described in International Publication WO 95/33848. Such polymer gas sensors usually rely on the detection of variations in their dc resistance (see, for example, J V Hatfield, P Neaves, P J Hicks, K Persaud and P Travers, Sensors & Actuators B, 18–19 (1994) 221–228). It is also possible to interrogate semiconducting organic polymers by applying ac electrical signal thereto and monitoring an electrical impedance quantity of the polymers, or variations in such an electrical impedance quantity, as a function of the frequency of the applied ac electrical signal (see, for example, British Patent GB 2203 553 and MEH Amrani, RM Dowdeswell, P A Payne and K C Persaud Proceedings of Eurosensors X, Vol. 2 (1996) pp 665–668). Using this latter technique, a single semiconducting organic polymer sensor may be used in place of a whole array. However, other gas sensing techniques, such as mass spectrometry, GC-MS, or spectroscopic techniques such as infra-red spectroscopy, might be employed.

It should be noted that simpler systems to those described above may also be employed. For example, a swab may be disposed within a suitable container and carrier gas flowed into and out of the containers. The swab may be disposed into a container having a liquid culturing medium, and sparging employed. Alternatively, a stop-flow technique can be used. In one embodiment, a swab is disposed in a container which is inflated or pressurised with a suitable carrier gas, possibly via a single needle through a septum. The positive pressure drives the flow, which may be released using a suitable valve. Before sampling, the swab may be left for a period of time to allow a headspace to develop.

FIG. 3 illustrates an analysis arrangement in which the flow through arrangement comprises a filter 31 on which microorganisms are collected from a sample flowing through the arrangement, introduced, possibly, from a syringe or vial 33. The microorganisms are trapped on the filter 31, which may be micromesh filter e.g. a 0.2 $\mu$m filter.

The flow through arrangement, after the flow has terminated, can be deployed as the headspace, a gas-senor probe being inserted, or the microorganisms may be washed off the filter, into a headspace, or the filter removed and deployed in a headspace of a gas sensor.

FIG. 4 illustrates an affinity column 41 performing the like function as the filter 31 of FIG. 3, microorganisms attaching to the affinity beads as by charge or an antibody. The column can be gas-analysed directly of the microorganisms eluted by e.g. a changed ionic strength wash solution.

The technique exemplified by FIGS. 3 and 4 offer the ability to remove the original matrix or carrier from the microorganisms under examination. This can be important to remove factors such as water or amines to which the sensors might be sensitive which could mask gases indicative of particular microorganisms or conditions of microorganisms.

The microorganisms to which this invention relates can include bacteria, yeast, fungi, viruses, prions or fragments of any of the above.

Swabs, filters and affinity beads can be constructed or treated so as to be selective to certain microorganisms (or against certain microorganisms), in which case gas analysis may be restricted to a go/no go test or arranged to give a fine resolution between microorganisms of a particular type.

The microorganisms may be gas analysed directly or after culturing or amplification.

What is claimed is:

1. A microorganism analysis means comprising:
   (a) a receptacle;
   (b) a cap sealing said receptacle and comprising a gas port;
   (c) a flow-through arrangement disposed in said receptacle and into which a microorganism-containing sample can be introduced, the flow-through arrangement comprising
      (i) a tubular member arranged to pass through said cap into said receptacle; and
      (ii) porous swab means disposed at one end of said tubular member and communicating therewith so that a gas flow may be flowed through said swab means and said tubular member, the gas flow carrying gases evolved from the microorganism-containing sample therein; and
   (d) a headspace connected or connectible to gas analysis means, wherein the headspace is connected to the flow-through arrangement so as to be affected by the sample.

2. The analysis means of claim 1, wherein the swab means comprises a polyethylene mesh.

3. The analysis means of claim 1, wherein the swab means comprises a porous ceramic.

4. The analysis means of claim 1, further comprising a culturing medium.

5. The analysis means of claim 4, wherein the culturing medium is a gel disposed on the surface of the swab means.

6. The analysis means of claim 5, wherein the gel is an agar gel.

7. The analysis means of claim 4, wherein the culturing medium comprises a liquid culting medium in which the swab means is disposed.

8. The analysis means of claim 1, wherein the swab means includes a layer of cotton wool or gauze.

9. A method of detecting microorganisms comprising the steps of:

providing microorganism analysis means comprising a tubular member and porous swab means disposed at one end of said tubular member and communicating therewith so that a gas flow may be flowed through said swab means and said tubular member;

obtaining a microorganism-containing sample using said swab means;

flowing a gas flow through said swab means and said tubular member, the gas flow carrying gases evolved from said microorganism-containing sample therein; and introducing said gas flow to gas analysis means.

10. A method according to claim 9, in which the gas analysis means comprises an array of gas sensors.

11. A method according to claim 9, in which the microorganism analysis means further comprises a receptacle into which said tubular member and swab means may be disposed.

12. A method according to claim 11, wherein the tubular member is disposed in a cap, the cap forming a seal with the receptacle when the tubular member and swab means are disposed therein.

13. A method according to claim 12, in which the cap comprises a gas port.

14. A method according to claim 13, in which the step of flowing a gas flow comprises carrying gases evolved from said microorganism-containing sample in the flow of gas which enters the receptacle via the gas port and exits the receptacle via the tubular member.

15. A method according to claim 13, in which the step of flowing a gas flow comprises carrying gases evolved from said microorganism-containing sample in the flow of gas which enters the receptacle via the tubular member and exits the receptacle via the gas port.

16. A method according to claim 15, in which the swab means is disposed in a quid culturing medium.

17. A method according to claim 9, in which the swab means comprises a polyethylene mesh.

18. A method according to claim 9, in which the swab means comprises a porous ceramic.

19. A method according to claim 9, in which the microorganism analysis means further comprises a culturing medium.

20. A method according to claim 19, in which the culturing medium is a gel disposed on a surface of the swab means.

21. A method according to claim 20, in which the gel is an agar gel.

22. A method according to claim 9, in which the swab means includes a layer of cotton wool or gauze.

* * * * *